United States Patent
Koerber et al.

(10) Patent No.: US 9,457,049 B2
(45) Date of Patent: *Oct. 4, 2016

(54) METHOD FOR GENERATING NITRIC OXIDE

(75) Inventors: Achim Gerhard Rolf Koerber, Eindhoven (NL); Rainer Hilbig, Eindhoven (NL)

(73) Assignee: KONKLIJKE PHILIPS N.V., Eindhoven (NL)

( * ) Notice: Subject to any disclaimer, the term of this patent is extended or adjusted under 35 U.S.C. 154(b) by 309 days.

This patent is subject to a terminal disclaimer.

(21) Appl. No.: 13/823,170

(22) PCT Filed: Sep. 12, 2011

(86) PCT No.: PCT/IB2011/053966
§ 371 (c)(1),
(2), (4) Date: Mar. 14, 2013

(87) PCT Pub. No.: WO2012/038853
PCT Pub. Date: Mar. 29, 2012

(65) Prior Publication Data
US 2013/0171272 A1    Jul. 4, 2013

(30) Foreign Application Priority Data
Sep. 22, 2010 (EP) .................... 10178293

(51) Int. Cl.
*C01B 21/30* (2006.01)
*A61K 33/00* (2006.01)
*C01B 21/24* (2006.01)

(52) U.S. Cl.
CPC ............ *A61K 33/00* (2013.01); *C01B 21/24* (2013.01)

(58) Field of Classification Search
CPC  C07C 51/316; C07C 55/14; A61K 2800/56; A61K 33/00; A61K 47/48015; A61K 8/19; A61K 8/26; A61L 15/18; A61L 15/44; A61L 2300/114; A61L 2300/802; A61L 29/02; A61L 29/16; A61L 31/028
See application file for complete search history.

(56) References Cited

U.S. PATENT DOCUMENTS 5,472,680 A * 12/1995 Reimer et al. ............. 423/405
5,692,495 A    12/1997 Sheu
5,711,859 A    1/1998  Caramel
6,296,827 B1   10/2001 Castor
6,328,941 B1   12/2001 Watzenberger et al.
6,500,398 B1   12/2002 Tagawa et al.
2001/0037810 A1 11/2001 Fine
2006/0269620 A1* 11/2006 Morris ................ A61K 8/19
                                                    424/684

FOREIGN PATENT DOCUMENTS

| AU | 2008232413 A1 | 10/2008 |
|---|---|---|
| CN | 1139420 A | 1/1997 |
| CN | 1280519 A | 1/2011 |
| DE | 19823748 A1 | 12/1999 |
| EP | 1903003 A1 | 3/2008 |
| WO | WO9317741 A1 | 9/1993 |
| WO | WO9520541 A1 | 8/1995 |
| WO | WO2006023616 A2 | 3/2006 |
| WO | WO2008118360 A1 | 10/2008 |

OTHER PUBLICATIONS

B.G. Reuben et al., "Thermal Decomposition of Nitrous Oxide", Transactions of the Faraday Society, Butterworths Scientific Publications Ltd. London, GB, vol. 55, Jan. 1, 1959, pp. 1543-1553.

J.A. Yagiela, "Health Hazards and Nitrous Oxide: A Time for Reappraisal", Anesthesia Progress, New York, NY, US, vol. 38, 1991, pp. 1-11.

M. Yoshida et al., "Combined Inhalation of Nitric Oxide and Oxygen in Chronic Obstructive Pulmonary Disease", American Journal of Respiratory and Critical Care Medicine, American Lung Association, New York, NY, US, vol. 155, No. 2, Feb. 1, 1997, pp. 526-529.

* cited by examiner

*Primary Examiner* — Audrea Buckley
(74) *Attorney, Agent, or Firm* — Michael W. Haas

(57) ABSTRACT

The present invention relates to a method for generating nitric oxide, in particular for therapeutic applications, which comprises the steps of: guiding a process gas into a reaction chamber (12), wherein the process gas comprises nitrous oxide in a carrier gas in a concentration in the range of $\leq 2$ vol-%, in particular in the range of $\geq 10^{-3}$ vol-% to $\leq 1$ vol-%, and heating the process gas to a temperature which is sufficiently high to enable a reaction of nitrous oxide to form nitric oxide, thereby forming a gas which at least partly comprises nitric oxide. This method allows generating nitric oxide without remarkable concentrations of toxic nitrogen oxides, in particular of nitrogen dioxide. The method according to the invention is particularly suitable for therapeutic applications.

10 Claims, 1 Drawing Sheet

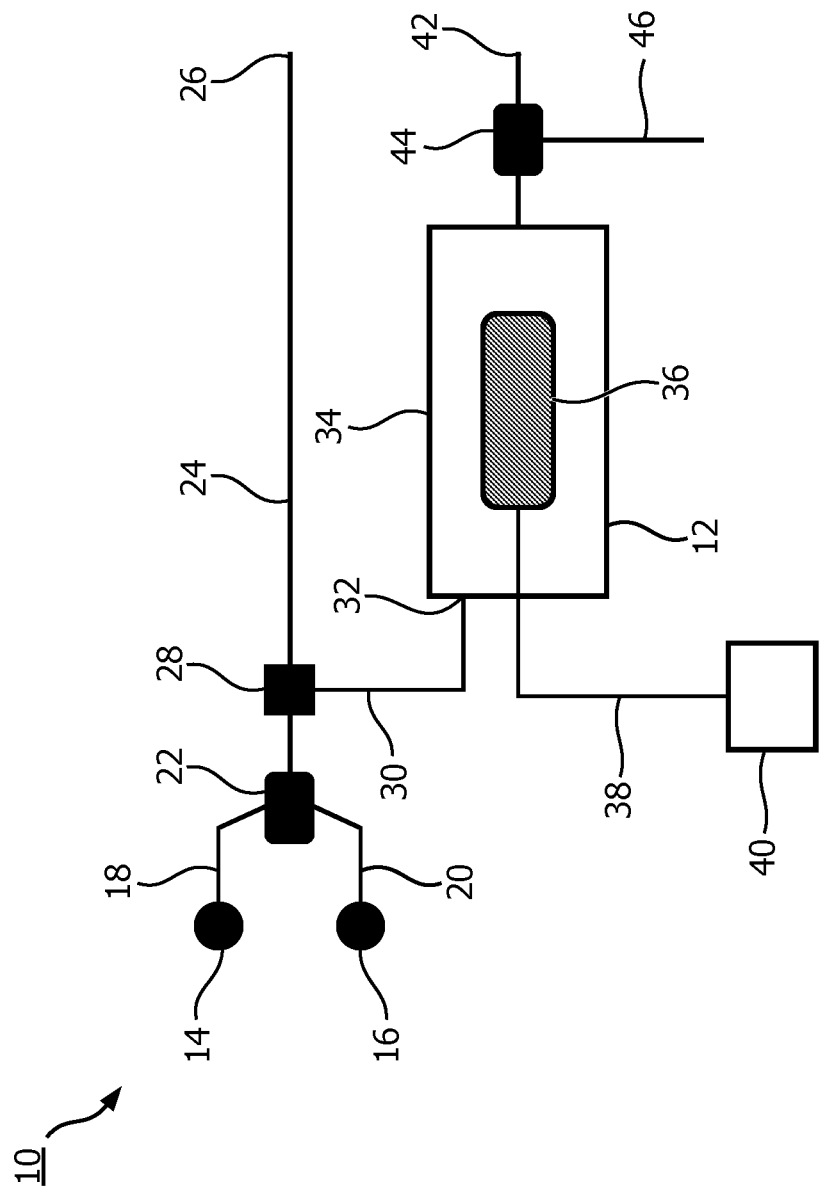

METHOD FOR GENERATING NITRIC OXIDE

FIELD OF THE INVENTION

The invention relates to the field of nitric oxide generation. More particularly, the invention relates to the field of nitric oxide generation for therapeutic applications.

BACKGROUND OF THE INVENTION

It is widely known to use nitric oxide (NO) in a variety of applications. Next to technical applications such as an intermediate in the Ostwald process for the synthesis of nitric acid from ammonia, especially several therapeutic applications using nitric oxide are known.

One of the most famous therapeutic applications of nitric oxide is the administration for neonates suffering from Persistent Pulmonary Hypertension (PPHN). However, many comparable or other therapeutic applications are known and discussed for the use of nitric oxide. As an example, nitric oxide is used by the endothelium of blood vessels to signal the surrounding smooth muscle to relax, thus resulting in widening the blood vessels and therefore increasing blood flow. This leads to nitric oxide being particularly applicable for the therapy of hypertension. Further exemplary applications for nitric oxide are directed towards improving lung function and treating or preventing bronchoconstriction, reversible pulmonary vasoconstriction, or for treating or preventing arterial restenosis resulting from excessive intimal hyperplasia. Apart from that, the administration of nitric oxide is particularly useful for treatment of infected tissue e.g. to kill bacteria. This application mostly involves topical delivery of a source of nitric oxide containing gas to a skin surface containing infected tissue.

The storage of nitric oxide for example in containers, or gas cylinders, respectively, may however cause difficulties. Due to the fact that nitric oxide tends to react with oxygen, even minor impurities of oxygen in the stored gas may cause the formation of nitrogen oxides in higher oxidation states, in particular the formation of toxic nitrogen dioxide ($NO_2$). Therefore, nitric oxide has only limited useful life time and may thus be stored only in a low concentration and for a limited time. For many applications, it is therefore preferred to generate nitric oxide in situ, i.e. directly before use.

The formation of nitric oxide may additionally lead to problems because of which several attempts to form nitric oxide are exercised. As an example, it is known to generate nitric oxide by using light being radiated on a chemical liquid leading to nitric oxide being evaporated. Further attempts are based on the formation of nitric oxide starting from air, for example by using a gas discharge. A gas discharge in air, however, generates not only nitric oxide, but also other compounds which bear health risks, e.g. ozone ($O_3$) and nitrogen dioxide ($NO_2$) may be formed.

A further attempt for generating nitric oxide is known from U.S. Pat. No. 6,238,941. Here, the main focus lies in the decomposition of nitrous oxide ($N_2O$) with a very high conversion efficiency. Starting from nitrous oxide as a precursor, nitric oxide is generated in particular by a thermal decomposition of nitrous oxide forming a nitric oxide comprising gas. The method is carried out without the use of a catalyst thereby applying high temperatures. The reacted gas mixture is then cooled by heat exchange. The reacted gas mixture comprises nearly no nitrous oxide but nitrogen as main component with a big amount of nitrogen oxides ($NO_x$).

One of the major drawbacks of the known methods for generating nitric oxide is the considerable formation of nitrogen oxides in higher oxidation states, in particular the formation of nitrogen dioxide. Due to the high toxicity of these nitrogen oxides in higher oxidation states, especially nitrogen dioxide, the generated gas mixture cannot be used directly, but further purification steps are required instead, in particular for therapeutic applications.

SUMMARY OF THE INVENTION

It is an object of the invention to provide a method for generating nitric oxide which overcomes at least one limitation as set forth above.

It is a further object of the invention to provide a method for generating nitric oxide in which the formation of nitrogen oxides in higher oxidation states, especially nitrogen dioxide, is effectively reduced or prevented.

It is a further object of the invention to provide a method for generating nitric oxide which is easy to perform and which may be used in therapeutic applications.

These objects are achieved by a method for generating nitric oxide, in particular for therapeutic applications, which comprises the steps of: guiding a process gas into a reaction chamber, wherein the process gas comprises nitrous oxide in a carrier gas in a concentration in the range of $\leq 2$ vol-%, in particular in the range of $\geq 10^{-3}$ vol-% to $\leq 1$ vol-%, and heating the process gas to a temperature which is sufficiently high to enable a reaction of nitrous oxide to form nitric oxide, thereby forming a gas which at least partly comprises nitric oxide.

The method according to the invention provides a safe and simple method to generate nitric oxide. The method according to the invention is particularly suitable for therapeutic applications.

According to the invention, the method starts from nitrous oxide as precursor. The usage of such a precursor is very beneficial. First of all, it is cheap leading to the method according to the invention being carried out in a cost-saving manner. Furthermore, nitrous oxide is an inert gas. This leads to the possibility of storing it safely for a substantially unlimited time e.g. in a gas cylinder or the like. During the storing time, there is no risk of undesired side products to be formed, especially there is no risk of the formation of toxic nitrogen oxides. Additionally, nitrous oxide as such is non-toxic in a wide range of concentrations. This offers the benefit that the method according to the invention may be carried out in situ even with respect to therapeutic applications. If some or even a major amount of nitrous oxide stays unreacted in the process gas, no health risk will appear by administering the formed nitric oxide comprising gas directly to a patient, because the nitrous oxide concentration will be $\leq 2$ vol-%.

Furthermore, no other radicals except nitric oxide and nitrogen dioxide are formed during the method according to the invention. This leads to the reaction being carried out in a well defined manner and with well defined products. Nearly no undesired side reaction will appear deteriorating the generated gas.

Additionally, it has to be noted that according to the invention, the concentration of nitrogen dioxide in the nitric oxide comprising gas is always below the security limit during every stage of the process. Therefore, there is no health risk even by applying the method according to the invention in situ with respect to therapeutic applications. The inventors have found that this security effect is obtained by the process gas comprising nitrous oxide in a carrier gas in a concentration in the range of ≤2 vol.-%, in particular in the range of ≥10$^{-3}$ vol-% to ≤1 vol-%.

With this regard, the concentration of nitrous oxide in the carrier gas may be adjusted before the gas mixture is inserted into the reaction chamber. The carrier gas and nitrous oxide may thus be mixed upstream the reaction chamber, e.g. in a mixing device, and guided into the reaction chamber afterwards, thereby having the desired concentration. It is furthermore possible to guide the carrier gas and nitrous oxide in the reaction chamber independently from each other, thereby mixing it in the reaction chamber and thus forming the process gas in the reaction chamber. However, it is preferred to guide the process gas into the reaction chamber as a combination of nitrous oxide and carrier gas in the desired concentration.

Additionally, due to the fact that the output concentration of nitric oxide is a certain fraction of the nitrous oxide start concentration, the obtained nitric oxide comprising gas offers a well defined concentration of nitric oxide. This concentration may further be very well adjusted by varying the process parameters. Said nitric oxide concentration may thus be adapted very well to a number of desired applications even by using a starting concentration of nitrous oxide as low as described above. In particular, the obtained concentration covers the range for therapeutic applications, or medical applications, respectively.

The step of heating the process gas to a temperature which is sufficiently high to enable a reaction of nitrous oxide to form nitric oxide thereby allows a conversion of nitrous oxide to nitric oxide without the use of a catalyst. This is especially advantageous as a catalyst most likely catalyzes undesired side reactions. In particular, the formation of nitrogen and oxygen will be activated by a catalyst.

In a preferred embodiment of the present invention, the process gas is heated to a temperature in a range of ≥1000K to ≤1500K. This reaction temperature allows nitrous oxide to be converted into nitric oxide with a sufficiently high conversion, which may be appropriate in a range of below 1%, without the need of a catalyst. Furthermore, these temperatures may very well be achieved by many conventional heating devices without the necessity of providing inadequate heat requirements with respect to the design of these heating devices, or the reaction chamber, respectively. In particular, these temperatures may very well be achieved in small devices being used for medical applications, e.g. home care applications.

In a further preferred embodiment of the present invention, an inert gas, in particular nitrogen, is used as carrier gas. The usage of an inert gas like nitrogen as carrier gas further inhibits the rate of the formation of nitrogen oxides in higher oxidation states. In particular, the formation of nitrogen dioxide may further be reduced or completely avoided.

In a still further preferred embodiment of the present invention, the water content in the process gas lies in a range of ≤1 vol-%. This enables the method according to the invention to be carried out substantially in the absence of water. A substantially water-free atmosphere may be important as water often inhibits the decomposition of nitrous oxide to nitric oxide and leads to the formation of nitrogen dioxide in high concentrations. This embodiment thus allows achieving appropriate conversions of nitrous oxide to nitric oxide at rather smooth reaction conditions.

In a still further preferred embodiment of the present invention, all surfaces in the reaction chamber are inert. This means that neither catalytic active surfaces, nor otherwise promoting, or activating surfaces are present in the reaction chamber, so that the rates of reactions at the walls are much smaller than reaction rates in the reaction chamber volume. This feature allows inhibiting several side reactions which may be performed in the presence of catalytic surfaces or promoting surfaces. In particular, side reactions as the formation of nitrogen and oxygen or reactions leading to the formation of nitrogen oxides in higher oxidation states, especially nitrogen dioxide, are inhibited. This leads to the advantage that no toxic nitrogen oxides are generated and furthermore the conversion of nitrous oxide to nitric oxide is not influenced in an undesired manner. Additionally, a very defined process is performed leading to well defined products in the nitric oxide comprising gas.

In a still further preferred embodiment of the present invention, the pressure in the reaction chamber during the reaction lies in a range of ≥0.1 bar to ≤20 bar, in particular at 1 bar. These pressure values allow suitable conversions of nitrous oxide to nitric oxide. Additionally, these pressures may be handled in a technical adequate way so that no complex pressurizing systems or reaction chambers are required.

In a further preferred embodiment of the present invention, the reaction time of the process gas lies in a range of ≥10 ms to ≤100 s, in particular in a range of ≥0.1 s to ≤30 s. These reaction times may lead to an adequate conversion at rather smooth reaction conditions. Additionally, the reaction times are short enough to generate a sufficiently high amount of nitric oxide comprising gas in a time scale which may be appropriate even for an in situ generation of nitric oxide, in particular for therapeutic applications.

In a still further preferred embodiment of the present invention, SATP flow rates of the process gas of ≥0.01 $L_{SATP}$/min to ≤10 $L_{SATP}$/min, in particular of 0.4 $L_{SATP}$/min are used wherein "$L_{SATP}$" means the amount of gas in 1 L volume at standard ambient temperature (25° C.; 298, 15K) and pressure (1 bar). This leads to the process gas having a sufficiently long reaction time even if the reaction chamber is designed in very small dimensions. The reaction time may be defined as $t=(V_r*p_r*298.15K)/(q^\ominus*1 bar*T_r)$, wherein $V_r$ means the volume of the reaction chamber at reaction temperature, $p_r$ means the reaction pressure, $T_r$ means the reaction temperature and $q^\ominus$ means the SATP flow rate. Furthermore, these flow rates are very well suited for an in situ generation of nitric oxide and to administer the formed gas directly without the need of (pre-)storing it.

In a still further preferred embodiment of the present invention, the formed nitric oxide comprising gas is cooled downstream the reaction chamber, in particular to room temperature. This allows the generated gas to be used directly, i.e. the usage of an in situ generation of nitric oxide comprising gas is improved. Furthermore, the generation of undesired side products, in particular nitrogen dioxide, downstream the reaction chamber is inhibited as these side products are mainly formed at elevated temperatures. The term "room temperature" thereby shall mean a temperature which is well suitable for a conventional use, in particular for therapeutic applications. In particular, the nitric oxide comprising gas is cooled down to a temperature which lies in a range of ≥15° C. to ≤35° C.

With this regard, it is especially preferred that the nitric oxide comprising gas is cooled to room temperature in a time range of ≤10 s, in particular ≤1 s. This ensures that no undesired side products are formed downstream the reaction chamber. Furthermore, these cooling speeds are in any case short enough to apply the method according to the invention to in situ applications.

BRIEF DESCRIPTION OF THE DRAWINGS

These and other aspects of the invention will be apparent from and elucidated with reference to the embodiments described hereinafter.

In the drawing:

FIG. 1 shows a schematically view of an arrangement designed for a method according to the invention.

DETAILED DESCRIPTION OF EMBODIMENTS

In FIG. 1, an arrangement 10 is schematically shown. The arrangement 10 is designed for carrying out a method for generating nitric oxide according to the invention, as will be apparent below. The arrangement 10 is particularly suitable for generating nitric oxide for therapeutic applications, especially for in situ generation.

The arrangement 10 comprises a reaction chamber 12 in which nitrous oxide is at least partly converted into nitric oxide. Therefore, a process gas which at least partly comprises nitrous oxide has to be guided into said reaction chamber 12. The arrangement 10 may thus comprise a first gas supply 14. The first gas supply 14 provides a source of nitrous oxide comprising gas. The nitrous oxide comprising gas may be pure nitrous oxide. In this case, the gas supply 14 may comprise a gas cylinder in which nitrous oxide is stored. Alternatively, the gas supply 14 may comprise a wall supply for nitrous oxide, or the like.

Due to the fact that according to the invention nitrous oxide is used in a limited concentration, the process gas not only comprises nitrous oxide but furthermore a carrier gas. This carrier gas may be an inert gas or an inert gas mixture. A preferred example for a carrier gas is nitrogen. However, it is furthermore possible to simply use air as carrier gas. It may be preferred to provide the carrier gas and nitrous oxide in one source, i.e. as a gas mixture. In this case, the first gas supply 14 is may comprise a source of nitrous oxide in a carrier gas, preferably nitrogen, wherein nitrous oxide is present in the carrier gas in the desired concentration. This allows the gas mixture to be used directly as process gas.

However, in an alternative aspect of the present invention, the carrier gas may be provided by a second gas supply 16. In this case, the stream of carrier gas as well as the stream of nitrous oxide both may be guided through tubes 18, 20 to a gas mixing device 22. In the gas mixing device 22, both respective streams are mixed to generate a process gas comprising nitrous oxide in the carrier gas in the desired concentration. The concentrations may be adjusted by providing respective flow controllers, in particular mass flow controllers, in the tubes 18, 20.

According to the invention, the process gas in the reaction chamber 12 has a concentration in the range of ≤2 vol-%, in particular in the range of ≥$10^{-3}$ vol-% to ≤1 vol-% in the carrier gas. This allows a reaction of nitrous oxide to nitric oxide without undesired side reactions. In particular, the formed nitric oxide is not oxidized to nitrogen oxides with higher oxidation states, e.g. nitrogen dioxide.

Due to the fact that according to the invention nitrous oxide and preferably an inert carrier gas like especially nitrogen are used for generating the process gas, there are only limited requirements with respect to gas supply. Neither nitrogen nor nitrous oxide tend to perform side reactions thereby forming undesired side products or changing the respective concentrations of the stored gases. Contrary thereto, theses gases may be stored and used over a substantially unlimited time. Even if nitrous oxide is provided in the carrier gas as a gas mixture in one gas source, there is no risk of nitrous oxide reacting in an undesired way during storing said gas mixture. Thus, the method according to the invention is particularly suitable for in situ applications of the nitric oxide comprising gas.

The generated stream of process gas may be guided through a tube 24 to an outlet 26 thereby forming a main flow. This main flow or a fraction of the main flow which is separated from said main flow is used for the method according to the invention as process gas. Thus, a junction 28 is provided in the tube 24 guiding a secondary flow through a tube 30 to a gas inlet 32 of the reaction chamber 12. The junction 28 may thus comprise a valve or the like allowing to separate a defined fraction of the main flow. The process gas may be conveyed from the gas source or the gas sources to the reaction chamber 12 by a suitable pump or just by the overpressure being present in the gas sources 14, and 16, respectively.

Preferably, the process gas enters the reaction chamber 12 with SATP flow rates lying in the range of ≥0.01 $L_{SATP}$/min to ≤10 $L_{SATP}$/min, in particular of 0.4 $L_{SATP}$/min. These flow rates are preferred for an appropriate reaction of the process gas and furthermore for a suitable usability of the generated nitric oxide comprising gas. Consequently, a flow controller may be arranged in the tube 30. In detail, reaction times of the process gas in the range of ≥0.1 s to ≤30 s are preferred to obtain a sufficient conversion.

In the reaction chamber 12, the process gas is heated to a temperature which is sufficiently high to enable a reaction of nitrous oxide to form nitric oxide, thereby forming a gas which at least partly comprises nitric oxide. Preferably, the process gas is heated up to a temperature in a range of ≥1000K to ≤1500K. Therefore, the reaction chamber 12 preferably comprises a housing 34 in which a heating device 36 is arranged. The heating device 36 may be any heating device which is appropriate to heat the process gas to the desired temperature. For example, the heating device 36 may comprise a lamp. In an exemplary manner only, the heating device 36 may be designed as a ceramic discharge metal halide (CDM) lamp. However, any suitable heating device 36 may be used. As a further example, the reaction chamber 12 may be designed as an oven. Appropriately, the heating device 36 is connected via a power supply line 38 to an energy source. 40.

The temperature range of ≥1000K to ≤1500K is high enough to allow a respective reaction of nitrous oxide without the need of a catalyst. In detail, it is preferred not to use catalytic or otherwise reaction promoting, or activating surfaces in the reaction chamber 12 and all parts connected with the latter, e.g. tubes and the like. Contrary thereto, it is preferred that all surfaces in the reaction chamber 12 are inert. The surfaces inside the reaction chamber 12 may thus be formed for example from high temperature resistant glass, for example quartz glass, or suited ceramic materials, for example alumina. These kinds of surfaces are completely stable against decomposition even at high temperatures like used in the present invention, and furthermore, they are inert against substances which may be used or formed at the method according to the invention. Furthermore, glass and ceramic materials have neither catalytic nor other promoting characteristics. Therefore, undesired side reactions, in particular the generation of nitrogen oxides like nitrogen dioxide are not activated.

Consequently, due to the design of the reaction chamber 12 with chemically inert surfaces, the method according to the invention may provide a well defined reaction of nitrous oxide to form nitric oxide. Substantially no undesired side reactions may appear leading to a well defined outcome of nitric oxide containing gas. In detail, substantially only the following reactions take place in the reaction chamber 12:

$$N_2O + M \rightarrow N_2 + O + M \qquad (1)$$

$$N_2O + O \rightarrow 2NO, \qquad (2)$$

$$N_2O + O \rightarrow N_2 + O_2, \qquad (3)$$

wherein M may be any gaseous molecule being present in the reaction chamber 12.

Downstream the reaction chamber 12, the generated nitric oxide comprising gas may be guided to the outside of the arrangement 10 through a tube 42. The generated gas may then be stored or used directly for the desired application.

Additionally, it is preferred that the water content in the process gas lies in a range of ≤1 vol-%. This may be important as water vapor may inhibit the desired reaction. The desired water content may be adjusted by using respectively dry gas sources. To ensure that the water content is not increased and furthermore to reduce the water content by using gas sources with a slightly higher water content, water vapor adsorbing substances may be provided, in particular in the tubes 18, 20, 24 and/or 30. As an example dried silica gel or dried zeolites or hygroscopic substances as e.g. phosphorus pentoxide may be used as a coating or as a plug inside the respective tubes upstream the reaction chamber 12.

To avoid further side reactions and particularly to avoid oxidation of nitric oxide downstream the reaction chamber 12, it may be preferable to cool the generated gas. Consequently, it may be preferred to arrange a cooling device 44 downstream the reaction chamber 12, in particular in the tube 42. Preferably, the generated gas is cooled down to room temperature. This cooling process should at best be performed very quickly. In particular, it is preferable that the gas is cooled in a time range lying at ≤10 s, especially ≤1 s. This is especially preferable if the concentration of nitric oxide lies in a range ≥0.1 vol-% or if oxygen is present in the process gas, e.g. if air is used as carrier gas. The cooling procedure thus helps to avoid undesired side reactions and thus to inhibit the formation of undesired side products, in particular of nitrogen dioxide. As known to those skilled in the art it may be advantageous to use a heat exchanger to heat the upstream gas and to cool the downstream gas, thereby enhancing the overall energy efficiency of the device.

The method according to the invention provides a flexible process which is very well adaptable to different applications of the formed nitric oxide comprising gas. Especially the concentration of nitric oxide in the nitric oxide comprising gas may be varied. Therefore, the generated nitric oxide comprising gas may be diluted with fresh air or another suitable gas. It may thus be preferred that the arrangement 10 comprises a gas inlet tube 46 which is connected to the outlet tube 42.

As an example, if the generated nitric oxide comprising gas shall be used in therapeutic applications, there are different parameters to be met. In detail, if the gas is used for respiratory applications, e.g. PPHN, quite high air flows in the range of 6 L/min with moderate concentrations of nitric oxide in the range of 20-40 ppm are required. As it may cause difficulties to heat such a secondary flow in the reaction chamber 12, a smaller secondary flow rate may be adjusted upstream the reaction chamber 12 and may be increased by introducing gas downstream the reaction chamber 12.

In contrast thereto, for wound healing applications, low gas flows in the region of 0.1 L/min and high concentrations of nitric oxide in the range of ≥100 ppm are required. The heating of these gas flows is not problematic, whereas the oxidation of nitric oxide to nitrogen dioxide may appear. According to the invention, this is however inhibited by using small concentrations of nitrous oxide in the process gas.

Especially according to therapeutic applications, the concentration of nitric oxide in the nitric oxide comprising gas may be sufficiently high in the range of below 100 ppm or several hundred ppm. This shows that process efficiency is not the main priority in this method. Contrary thereto, the main focus lies on a well defined concentration of the generated gas and additionally on an avoidance of appreciable concentrations of toxic gases like nitrogen dioxide. The concentration of nitric oxide may be adjusted by varying the process parameters, i.e. conversion temperature, heating time, cooling time, etc. However, from the above it is apparent that it is especially preferable to work at low total pressures, preferably in the range of ≥0.1 bar to ≤20 bar, in particular at 1 bar, and at high temperatures, preferably in a range of ≥1000K to ≤1500K. It is thus possible to only decompose, or react, respectively, a very small fraction of the nitrous oxide being present in the process gas. Especially for therapeutic applications, a conversion of 2% may be sufficient. Due to the fact that nitrous oxide does not cause a toxicity problem in a wide concentration range, the method according to the invention may be used in situ even for therapeutic applications with said small conversions.

In the following, exemplary reactions according to the method according to the invention are described.

TABLE 1

Exemplary reactions according to the invention

| # | Carrier Gas | Reaction $c(N_2O)$ [%] | Conditions Flow Rate [L/min] | Temperature [K] | Reacted c(NO) [ppm] | Gas $c(NO_2)$ [ppm] |
|---|---|---|---|---|---|---|
| 1 | $N_2$ | 1 | 0.4 | 1100 | 63 | 2.7 |
| 2 | $N_2$ | 0.5 | 0.4 | 1100 | 18 | 0.9 |
| 3 | air | 1 | 0.4 | 1100 | 65 | 10 |
| 4 | air | 0.5 | 0.4 | 1100 | 20 | 4 |
| 5 | air | $5 * 10^{-4}$ | 0.6 | 1223 | 66 | 3.1 |
| 6 | $N_2$ | $5 * 10^{-4}$ | 0.6 | 1223 | 42 | 1.3 |
| 7 | $N_2$ | $10^{-3}$ | 0.6 | 1223 | 72 | 2.0 |
| 8 | $N_2$ | $5 * 10^{-4}$ | 0.6 | 1273 | 57 | 1.6 |

Examples 1 to 4 were carried out using a CDM lamp as heater in a blackened outer bulb and using 70 W power. The volume of said heater was about 9 cm³. Examples 5 to 8 were carried out using a tubular oven, the heated part of which comprises a volume of 157 cm³.

From examples 1 and 2 it can be seen that nitric oxide may be generated in sufficiently high concentrations, in particular in a range of ≥10 ppm, which is particularly suitable for therapeutic applications. The concentration ratio $NO_2/NO$ can furthermore be lower than 1/10, which is especially preferable to exclude safety risks associated with high nitrogen dioxide concentrations. Additionally, only a small fraction (~2%) of the nitrous oxide is decomposed in example 1, due to the fact that the heater, i.e. the outer bulb volume is quite low and the reaction time is thus rather short (~0.4 s). This however is not dramatic due to the fact that nitrous oxide is not harmful in these amounts.

The examples 3 and 4 are comparable to the examples 1 and 2. However, as air is used as carrier gas, the nitrogen dioxide amount was raised. The formation of nitrogen dioxide was caused by reactions of the hot nitric oxide with oxygen and moisture. However, even by using air as carrier gas it was still possible to provide a concentration ratio of $NO_2/NO$ which is lower than 1/5 with small nitric oxide concentrations which as well is acceptable for therapeutic applications.

The examples 5 to 8 are carried out with a significant decrease of the nitrous oxide concentration. It can clearly be seen that the concentration ratio $NO_2/NO$ is below 1/20 even if air is used as carrier gas. In case nitrogen is used as carrier gas, this concentration ratio may be even furthermore improved.

Additionally, in the examples 5 to 8 by using an oven resulting in a longer reaction time, conversions between 81% (examples 5-7) and 97% (example 8) are achieved.

From the above, it can be seen that the method according to the invention is suitable for generating nitric oxide starting from nitrous oxide, especially for therapeutic applications.

However, the respective parameters of the method according to the invention may be adapted to the desired applications. In detail, the parameters which may be adapted comprise temperature, volume of the reaction chamber and gas flow resulting in a defined reaction time, and the initial nitrous oxide concentration of the process gas.

The reaction time is thereby one essential parameter. The inventors have found that the conversion efficiencies from nitrous oxide to nitric oxide are very low at short reaction times and it is difficult to adjust the resulting nitric oxide concentration reliably. Generally, long reaction times and additionally high temperatures might be necessary to realize high conversions.

However, if the reaction time is chosen to be rather short, then the ratio $nNO_2/nNO$ can be improved by increasing the reaction temperature or lowering the total pressure inside the reaction chamber.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for generating nitric oxide for therapeutic applications comprising:
   guiding a process gas into a reaction chamber, wherein the process gas comprises nitrous oxide in a carrier gas in a concentration in the range of ≤2 vol-%;
   heating the process gas to a temperature which is sufficiently high to enable a reaction of nitrous oxide to form nitric oxide;
   forming a gas which at least partly comprises nitric oxide; and
   cooling the formed gas at least partially comprising nitric oxide to room temperature with a cooling device comprising a heat exchanger downstream from the reaction chamber.

2. The method of claim 1, wherein the process gas is heated to a temperature in a range of ≥1000K to ≤1500K.

3. The method of claim 1, wherein an inert gas is used as carrier gas.

4. The method of claim 1, further comprising, prior to guiding the process gas into the reaction chamber, guiding the process gas through a tube coated with a water vapor adsorbing substance including one or more of dried silica gel or phosphorus pentoxide such that a water content in the process gas lies in a range of ≤1 vol-% before being guided into the reaction chamber.

5. The method of claim 1, wherein all surfaces in the reaction chamber are inert, the inert surfaces comprising quartz glass or alumina.

6. The method of claim 1, wherein the pressure in the reaction chamber during the reaction lies in a range of ≥0.1 bar to ≤20 bar.

7. The method of claim 1, wherein the reaction time of the process gas lies in a range of ≥10 ms to ≤100 s.

8. The method of claim 1, wherein SATP flow rates of the process gas of ≥0.01 $L_{SATP}$/min to ≤10 $L_{SATP}$/min are used.

9. The method of claim 1, wherein the formed nitric oxide gas is cooled downstream from the reaction chamber.

10. The method of claim 1, wherein the nitric oxide comprising gas is cooled to room temperature in a time range of ≤10 s.

* * * * *